(12) United States Patent
Peffly et al.

(10) Patent No.: US 8,623,341 B2
(45) Date of Patent: Jan. 7, 2014

(54) PERSONAL CARE COMPOSITIONS CONTAINING CATIONICALLY MODIFIED STARCH AND AN ANIONIC SURFACTANT SYSTEM

(75) Inventors: Marjorie Mossman Peffly, Cincinnati, OH (US); Salvador Pliego, Mason, OH (US); James Anthony Staudigel, Cincinnati, OH (US); Yonas Gizaw, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 1790 days.

(21) Appl. No.: 11/169,827

(22) Filed: Jun. 29, 2005

(65) Prior Publication Data

US 2006/0002880 A1 Jan. 5, 2006

Related U.S. Application Data

(60) Provisional application No. 60/585,152, filed on Jul. 2, 2004.

(51) Int. Cl.
*A61K 8/00* (2006.01)
(52) U.S. Cl.
USPC ............... 424/70.1; 424/70.11; 424/70.13; 424/70.22; 424/401
(58) Field of Classification Search
None
See application file for complete search history.

(56) References Cited

U.S. PATENT DOCUMENTS

| | | | |
|---|---|---|---|
| 1,110,756 A | 9/1914 | Duryea | |
| 3,986,890 A | 10/1976 | Richter | |
| 4,052,226 A | 10/1977 | Verbanac | |
| 5,801,116 A * | 9/1998 | Cottrell et al. | 502/404 |
| 5,977,038 A | 11/1999 | Birtwistle et al. | |
| 6,153,569 A | 11/2000 | Halloran | |
| 6,344,183 B2 * | 2/2002 | Paul et al. | 424/47 |
| 6,365,140 B1 | 4/2002 | Melby | |
| 6,964,720 B2 | 11/2005 | Schneider | |
| 7,211,268 B2 | 5/2007 | Dubief et | |
| 2001/0031270 A1 | 10/2001 | Douin | |
| 2002/0012646 A1 | 1/2002 | Royce | |
| 2002/0034487 A1 | 3/2002 | Maubru | |
| 2003/0108507 A1 | 6/2003 | Clipson | |
| 2003/0129210 A1 | 7/2003 | Chowdhary | |
| 2004/0037794 A1 | 2/2004 | Dubief | |
| 2004/0077510 A1 * | 4/2004 | Lazzeri et al. | 510/130 |
| 2004/0105833 A1 | 6/2004 | Fack | |
| 2005/0069511 A1 | 3/2005 | Magnet | |

FOREIGN PATENT DOCUMENTS

| | | |
|---|---|---|
| AU | 200114496 B2 | 6/2001 |
| DE | 10128799 A1 | 7/2001 |
| EP | 0577519 B1 | 4/1996 |
| EP | 0610407 B1 | 8/1996 |
| EP | 0853941 A2 | 7/1998 |
| EP | 1051967 A2 | 11/2000 |
| EP | 0332027 B1 | 2/2001 |
| EP | 1054656 B1 | 4/2003 |
| EP | 1380284 A1 | 1/2004 |
| JP | 54086-629 | 12/1977 |
| JP | 55043-138 | 9/1978 |
| JP | 07-017826 | 1/1995 |
| JP | 07-017827 | 1/1995 |
| JP | 07277931 A | 10/1995 |
| WO | WO-93/08787 A2 | 5/1993 |
| WO | WO-97/23193 A1 | 7/1997 |
| WO | WO-97/42225 A1 | 11/1997 |
| WO | WO-98/18434 A1 | 5/1998 |
| WO | WO-01/39721 A2 | 6/2001 |
| WO | WO-02/22091 A2 | 3/2002 |
| WO | WO-03/084486 A1 | 4/2002 |
| WO | WO-03/084487 A1 | 4/2002 |
| WO | WO-2004/014326 A1 | 2/2004 |

* cited by examiner

*Primary Examiner* — Lezah Roberts
*Assistant Examiner* — Nannette Holloman
(74) *Attorney, Agent, or Firm* — Angela K. Haughey

(57) ABSTRACT

Personal care compositions comprise (a) from about 0.01 wt. % to about 10 wt. % of a water-soluble cationically modified starch polymer, wherein said water-soluble cationically modified starch polymer has a molecular weight from about 1,000 to about 200,000 and a charge density from about 0.7 meq/g to about 7 meq/g; (b) from about 5 wt. % to about 50 wt. % of an anionic surfactant system, said anionic surfactant system comprising at least one anionic surfactant and having an ethoxylate level and an anion level, (i) wherein said ethoxylate level is from about 1 to about 6, and (ii) wherein said anion level is from about 1 to about 6; and (c) a cosmetically acceptable medium. Personal care compositions as described above further comprise from about 0.01 wt. % to about 10 wt. % of one or more oily conditioning agents. Methods of treating hair or skin comprise applying the personal care compositions as described above to the hair or skin and rinsing the hair or skin.

14 Claims, No Drawings

PERSONAL CARE COMPOSITIONS CONTAINING CATIONICALLY MODIFIED STARCH AND AN ANIONIC SURFACTANT SYSTEM

CROSS REFERENCE

This application claims the benefit of U.S. Provisional Application No. 60/585,152 (Case 9707P), filed, Jul. 2, 2004.

FIELD OF THE INVENTION

The present invention relates to personal care compositions comprising a cationically modified starch polymer. More particularly, the present invention relates to personal care compositions comprising an anionic surfactant system and a cationically modified starch polymer. In one aspect, the present invention relates to personal care compositions as described above which further comprise one or more oily conditioning agents.

BACKGROUND OF THE INVENTION

Shampoo compositions comprising various combinations of detersive surfactants and conditioning agents are known. These products typically comprise an anionic detersive surfactant in combination with a conditioning agent such as silicone, hydrocarbon oil, fatty esters, or combinations thereof. These products have become more popular among consumers as a means of conveniently obtaining hair or skin conditioning and cleansing performance all from a single personal care product.

However, many shampoo compositions do not provide sufficient deposition of conditioning agents onto hair and skin during the cleansing process. Without such deposition, large proportions of conditioning agent are rinsed away during the cleansing process and, therefore, provide little or no conditioning benefit. Without sufficient deposition of the conditioning agent on the hair and skin, relatively high levels of conditioning agents may be needed in the personal cleansing composition to provide adequate conditioning performance. However, high levels of a conditioning agent can increase raw material costs, reduce lathering, and present product stability concerns.

Obtaining good deposition of a conditioning agent is further complicated by the action of detersive surfactants in the shampoo composition. Detersive surfactants are designed to carry away or remove oil, grease, dirt, and particulate matter from the hair and skin. As a result, the detersive surfactants can interfere with deposition of the conditioning agent and can remove both deposited and non-deposited conditioning agent during rinsing. Consequently, after rinsing, the deposition of the conditioning agent onto the hair and skin is reduced, which, in turn, reduces conditioning performance.

One method for improving deposition of a conditioning agent involves the use of certain cationic deposition polymers. Typically, these cationic deposition polymers are natural polymers, such as cellulosic or guar polymers that have been modified with cationic substituents. Sufficient deposition of conditioning agents can result from selecting a cationic deposition polymer with sufficient charge density and molecular weight in combination with an optimized surfactant system. However, to achieve this sufficient deposition in shampoo or body wash compositions, generally, the molecular weight of the cellulosic or guar deposition polymers is well above 200,000. High molecular weight cationic starches also have been available for a number of years. However, high molecular weight starches do not provide an appropriate level of wet conditioning or detangling of wet hair. Thus, a need still exists to provide both adequate wet conditioning and a high level of conditioning active deposition with a low cost cationic or amphoteric polymer.

It is also desirable that shampoo compositions which deliver conditioning agents do not result in a cleaning tradeoff, buildup, or reduced volume of the intended hair style, and, further, that the shampoos are storage stable. Previous attempts to achieve sufficient conditioning performance in shampoos have been made using dispersed droplets of silicone oil in combination with depositing high levels of high molecular weight polymer. However, these attempts result in buildup of polymer and conditioning agents, which potentially can result in a reduction of hairstyle volume. Thus, a need still exists to provide sufficient conditioning performance without a reduction in hairstyle volume with a low cost cationic or amphoteric polymer in a shampoo composition.

Accordingly, there is a continuing need for a personal cleansing composition which delivers superior conditioning benefits to hair and/or skin with a low cost cationic or amphoteric polymer without buildup effects or a reduced cleansing performance.

SUMMARY OF THE INVENTION

The present invention is directed to a personal care composition comprising: (a) from about 0.01 wt. % to about 10 wt. % of a water-soluble cationic cationically modified starch polymer, wherein said water-soluble cationically modified starch polymer has a molecular weight from about 1,000 to about 200,000 and a charge density from about 0.7 meq/g to about 7 meq/g; (b) from about 5 wt. % to about 50 wt. % of an anionic surfactant system, said anionic surfactant system comprising at least one anionic surfactant and having an ethoxylate level and an anion level, (i) wherein said ethoxylate level is from about 1 to about 6, and (ii) wherein said anion level is from about 1 to about 6; and (c) a cosmetically acceptable medium.

Additionally, the present invention is directed to a personal care composition as described above further comprising from about 0.01 wt. % to about 10 wt. % of one or more oily conditioning agents.

The present invention is also directed to a method of treating hair or skin comprising the steps of applying the personal care composition as described above to the hair or skin and rinsing the hair or skin.

The combination of the cationically modified starch polymer with the anionic surfactant system of the present invention in personal care compositions provides enhanced deposition of conditioning agents to hair and/or skin without reducing cleansing performance. It is believed that certain specific anionic surfactant systems as described by the ethoxylate and anion levels maximize a conditioning benefit of a polymer via maximization of coacervate formation. Coacervates, without being limited to a particular theory, provide improved hair and skin conditioning without any additional conditioning actives. Further, when dispersed conditioning agent droplets are added to the system, the coacervate provides an improved mechanism for conditioning agent deposition.

DETAILED DESCRIPTION OF THE INVENTION

While the specification concludes with claims that particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level, and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "charge density", as used herein, refers to the ratio of the number of positive charges on a monomeric unit of which a polymer is comprised to the molecular weight of said monomeric unit. The charge density multiplied by the polymer molecular weight determines the number of positively charged sites on a given polymer chain.

The term "polymer" as used herein shall include materials whether made by polymerization of one type of monomer or made by two (i.e., copolymers) or more types of monomers.

The term "solid particle" as used herein means a particle that is not a liquid or a gas.

The term "water-soluble" as used herein, means that the polymer is soluble in water in the present composition. In general, the polymer should be soluble at 25° C. at a concentration of at least 0.1% by weight of the water solvent, preferably at least 1%, more preferably at least 5%, most preferably at least 15%.

The term "water-insoluble" as used herein, means that a compound is not soluble in water in the present composition. Thus, the compound is not miscible with water.

The personal care compositions of the present invention comprise a cationically modified starch polymer, an anionic surfactant system, and a cosmetically acceptable medium. Each of these essential components, as well as preferred or optional components, is described in detail hereinafter.

A. Cationically Modified Starch Polymer

The personal care compositions of the present invention comprise water-soluble cationically modified starch polymers. As used herein, the term "cationically modified starch" refers to a starch to which a cationic group is added prior to degradation of the starch to a smaller molecular weight, or to a starch to which a cationic group is added after modification of the starch to a desired molecular weight. The definition of the term "cationically modified starch" also includes amphoterically modified starch. The term "amphoterically modified starch" refers to a starch hydrolysate to which a cationic group and an anionic group are added.

The personal care compositions of the present invention comprise cationically modified starch polymers at a range of about 0.01% to about 10%, and more preferably from about 0.05% to about 5%, by weight of the composition.

The cationically modified starch polymers for use in the personal care compositions of the present invention have a molecular weight from about 1,000 to about 200,000. In one embodiment of the present invention, the cationically modified starch polymers have a molecular weight from about 5,000 to about 100,000. As used herein, the term "molecular weight" refers to the weight average molecular weight. The weight average molecular weight may be measured by gel permeation chromatography ("GPC") using an Alliance HPLC (Waters 2695 Separation Module) with two hydrogel columns in series (Waters Ultrahydrogel Linear 6-13 um, 7.8×300 nm GPC column, part number 011545) at a column temperature of 30° C. and at a flow rate of 0.9 ml/min, and using a Viscotek Model 300 TDA (triple detector array), light scattering detector (single angle, 90°), viscosity detector, and refractive index detector, all at detector temperatures of 30° C., with a method created by using pullulan narrow standard P-800 from American Polymer Standards Corporation ($M_w$=788,000), with an injection volume of 25 to 100 μl, and using a dn/dc of 0.147. Additional details on measuring the weight average molecular weight according to a GPC method are described in U.S. Publication No. 2003/0154883 A1, entitled "Non-Thermoplastic Starch Fibers and Starch Composition for Making Same."

The personal care compositions of the present invention include cationically modified starch polymers which have a charge density from about 0.7 meq/g to about 7 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., *Cationic Starches in Modified Starches: Properties and Uses*, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers of the present invention generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy ("$^1$H NMR") methods well known in the art. Suitable $^1$H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, *Carbohydrate Research,* 160 (1987), 57-72; and "An Approach to the Structural Analysis of Oligosaccharides by NMR Spectroscopy", J. Howard Bradbury and J. Grant Collins, *Carbohydrate Research,* 71, (1979), 15-25.

The cationically modified starch polymers for use in the personal care compositions of the present invention may comprise maltodextrin. Thus, in one embodiment of the present invention, the cationically modified starch polymers may be further characterized by a Dextrose Equivalance ("DE") value of less than about 35, and more preferably from about 1 to about 20. The DE value is a measure of the reducing equivalence of the hydrolyzed starch referenced to dextrose and expressed as a percent (on dry basis). Starch completely hydrolyzed to dextrose has a DE value of 100, and unhydrolyzed starch has a DE value of 0. A suitable assay for DE value includes one described in "Dextrose Equivalent", *Standard*

*Analytical Methods of the Member Companies of the Corn Industries Research Foundation*, 1st ed., Method E-26. Additionally, the cationically modified starch polymers of the present invention may comprise a dextrin. Dextrin is typically a pyrolysis product of starch with a wide range of molecular weights.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

In one embodiment of the present invention, cationically modified starch polymers are selected from degraded cationic maize starch, cationic tapioca, cationic potato starch, and mixtures thereof. In another embodiment, cationically modified starch polymers are cationic corn starch.

The starch, prior to degradation or after modification to a smaller molecular weight, may comprise one or more additional modifications. For example, these modifications may include cross-linking, stabilization reactions, phophorylations, and hydrolyzations. Stabilization reactions may include alkylation and esterification.

The cationically modified starch polymers in the present invention may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance$\geq$80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in compositions of the present invention is available from known starch suppliers. Also suitable for use in the present invention is nonionic modified starch that could be futher derivatized to a cationically modified starch as is known in the art. Other suitable modified starch starting materials may be quaternized, as is known in the art, to produce the cationically modified starch polymer suitable for use in the invention.

B. Anionic Surfactant System—Ethoxylate Level and Anion Level

The personal care compositions of the present invention comprise an anionic surfactant system. The anionic surfactant system is included to provide cleaning performance to the composition. The anionic surfactant system comprises at least one anionic surfactant, and optionally an amphoteric surfactant, a zwitterionic surfactant, a cationic surfactant, a nonionic surfactant, or a combination thereof. Such surfactants should be physically and chemically compatible with the essential components described herein, or should not otherwise unduly impair product stability, aesthetics, or performance.

Suitable anionic surfactant components for use in the personal care composition herein include those that are known for use in hair care or other personal care compositions. The concentration of the anionic surfactant system in the personal care composition should be sufficient to provide the desired cleaning and lather performance, and generally ranges from about 5% to about 50%, preferably from about 8% to about 30%, more preferably from about 10% to about 25%, by weight of the composition.

In considering the performance characteristics of a personal care composition, such as coacervate formation, wet conditioning performance, dry conditioning performance, and conditioning ingredient deposition on hair, it is necessary to optimize the levels and types of surfactants in order to maximize the performance potential of polymer systems. The anionic surfactant system for use in the personal care compositions of the present invention has an ethoxylate level and an anion level, wherein the ethoxylate level is from about 1 to about 6, and wherein the anion level is from about 1 to about 6. The combination of such an anionic surfactant system with the cationically modified starch polymers of the present invention in personal care compositions provide enhanced deposition of conditioning agents to hair and/or skin without reducing cleansing performance.

An optimal ethoxylate level can be calculated based on the stoichiometry of the surfactant structure, which in turn is based on a particular molecular weight of the surfactant where the number of moles of ethoxylation is known. Likewise, given a specific molecular weight of a surfactant and an anionization reaction completion measurement, the anion level can be calculated. Analytical techniques have been developed to measure ethoxylation or anionization within surfactant systems. The Level of Ethoxylate and the Level of Anion representative of a particular surfactant system are calculated from the percent ethoxylation and percent anion of individual surfactants in the following manner:

Level of Ethoxylate in a composition=percent ethoxylation multiplied by percent active ethoxylated surfactant (based upon the total weight of the composition).

Level of Anion in a composition=percent anion in ethoxylated surfactant multiplied by percent active ethoxylated surfactant (based upon the total weight of the composition) plus percent anion in non-ethoxylated surfactant multiplied by percent active non-ethoxylated surfactant (based upon the total weight of the composition).

If a composition comprises two or more surfactants having different respective anions (e.g., surfactant A has a sulfate group and surfactant B has a sulfonate group), the Level of Anion in the composition is the sum of the molar levels of each respective anion as calculated above.

Sample Calculation:

Example 1 shows an ethoxylated surfactant that contains 0.294321% ethoxylate and 0.188307% sulfate as the anion and a non-ethoxylated surfactant that contains 0.266845% sulfate as an anion. Both surfactants are 29% active.

Level of Ethoxylate in Example 1=0.294321 multiplied by 14 (% active ethoxylated surfactant). Thus, the Level of Ethoxylate in the composition of Example 1 is approximately 4.12.

Level of Anion in Example 1=0.188307 multiplied by 14 (% active ethoxylated surfactant) plus 0.266845 multiplied by 2 (% active non-ethoxylated surfactant). Thus, the Level of Anion in the composition of Example 1 is approximately 3.17.

The anionic surfactant system comprises at least one anionic surfactant comprising an anion selected from the group consisting of sulfates, sulfonates, sulfosuccinates, isethionates, carboxylates, phosphates, and phosphonates. Preferably, the anion is a sulfate.

Preferred anionic surfactants suitable for use in the personal care compositions are alkyl sulfates and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from about 1 to about 10, and M is a cation such as ammonium, an alkanolamine such as triethanolamine, a monovalent metal such as sodium and potassium, or a polyvalent metal cation such as magnesium and calcium. Solubility of the surfactant will depend upon the particular anionic surfactants and cations chosen.

Preferably, R has from about 8 to about 18 carbon atoms, more preferably from about 10 to about 16 carbon atoms, even more preferably from about 12 to about 14 carbon atoms, in both the alkyl sulfates and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with from about 0 to about 10, preferably from about 2 to about 5, more preferably about 3, molar proportions of ethylene oxide, and the resulting mixture of molecular species having, for example, an average of 3 moles of ethylene oxide per mole of alcohol is sulfated and neutralized.

Specific non-limiting examples of alkyl ether sulfates which may be used in the personal care compositions of the present invention include sodium and ammonium salts of coconut alkyl triethylene glycol ether sulfate, tallow alkyl triethylene glycol ether sulfate, and tallow alkyl hexa-oxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide. Such a mixture also comprises from about 0% to about 20% by weight $C_{12-13}$ compounds; from about 60% to about 100% by weight of $C_{14-15-16}$ compounds; from about 0% to about 20% by weight of $C_{17-18-19}$ compounds; from about 3% to about 30% by weight of compounds having a degree of ethoxylation of 0; from about 45% to about 90% by weight of compounds having a degree of ethoxylation from about 1 to about 4; from about 10% to about 25% by weight of compounds having a degree of ethoxylation from about 4 to about 8; and from about 0.1% to about 15% by weight of compounds having a degree of ethoxylation greater than about 8.

Another suitable class of anionic surfactants are the water-soluble salts of the organic, sulfuric acid reaction products of the general formula $R_1SO_3\text{-}M$ wherein $R_1$ is chosen from the group consisting of a straight or branched chain, saturated aliphatic hydro-carbon radical having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms, and a sulfonating agent e.g., $SO_3$, $H_2SO_4$, oleum, obtained according to known sulfonation methods, including bleaching and hydrolysis. Preferred are alkali metal and ammonium sulfonated $C_{12-18}$-n-paraffins.

Examples of anionic surfactants for use in the personal care compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, and combinations thereof.

Still other suitable anionic surfactants are the reaction products of fatty acids esterified with isethionic acid and neutralized with sodium hydroxide where, for example, the fatty acids are derived from coconut oil or palm kernel oil, and sodium or potassium salts of fatty acid amides of methyl tauride where, for example, the fatty acids are derived from coconut oil or palm kernel oil.

Other anionic surfactants suitable for use in the shampoo compositions are the succinnates, examples of which include disodium N-octadecylsulfosuccinate, disodium lauryl sulfosuccinate, diammonium lauryl sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, and dioctyl esters of sodium sulfosuccinic acid.

Other suitable anionic surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The alpha-olefins from which the olefin sulfonates are derived are mono-olefins having from about 10 to about 24 carbon atoms, preferably from about 12 to about 16 carbon atoms. Preferably, they are straight chain olefins.

Another class of anionic surfactants suitable for use herein is the beta-alkyloxy alkane sulfonates. These surfactants conform to the formula:

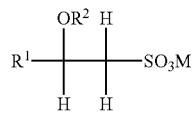

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described.

In addition to the sulfates, isethionates, sulfonates, sulfosuccinates described above, other potential anions for the anionic surfactant include phosphonates, phosphates, and carboxylates.

The personal care compositions of the present invention may also include one or more additional surfactants selected from the group consisting of amphoteric surfactants, zwitterionic surfactants, cationic surfactants, and nonionic surfactants. Suitable amphoteric, zwitterionic, cationic, or nonionic surfactants for use in the personal care compositions herein include those which are known for use in hair care or other personal care compositions. The concentration of such surfactants preferably ranges from about 0.5% to about 20%, preferably from about 1% to about 10%, by weight of the composition. Non-limiting examples of suitable surfactants are described in U.S. Pat. Nos. 5,104,646 and 5,106,609, both to Bolich, Jr. et al.

Non-limiting examples of other surfactants suitable for use in the personal care compositions are described in McCutcheon's, Emulsifiers and Detergents, 1989 Annual, published by M. C. Publishing Co.

C. Cosmetically Acceptable Medium

The personal care compositions of the present invention comprise a cosmetically acceptable medium. The level and species of the medium are selected according to the compatibility with other components and other desired characteristic of the product. Generally, the cosmetically acceptable medium is present in an amount from about 20% to about 95% by weight of the composition. A cosmetically acceptable medium may be selected such that the composition of the present invention may be in the form of, for example, a pourable liquid, a gel, a paste, a dried powder, or a dried film.

Cosmetically acceptable mediums useful in the present invention include water and water solutions of lower alkyl alcohols. Lower alkyl alcohols useful herein are monohydric alcohols having 1 to 6 carbons, and preferably are selected from ethanol and isopropanol.

The pH of the present composition, measured neat, is preferably from about 3 to about 9, more preferably from about 4 to about 8. Buffers and other pH-adjusting agents can be included to achieve the desirable pH.

D. Oily Conditioning Agent

In a preferred embodiment of the present invention, the personal care compositions comprise one or more oily conditioning agents. Oily conditioning agents include materials which are used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The oily conditioning agents useful in the compositions of the present invention typically comprise a water-insoluble, water-dispersible, non-volatile, liquid that forms emulsified, liquid particles. Suitable oily conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

One or more oily conditioning agents are typically present at a concentration from about 0.01% to about 10%, preferably from about 0.1% to about 8%, more preferably from about 0.2% to about 4%, by weight of the composition.

In a preferred embodiment of the compositions of the present invention, the ratio of oily conditioning agent to cationic hydrolyzed starch polymer is at least about 2:1.

1. Silicone Conditioning Agent

The oily conditioning agents of the compositions of the present invention are preferably a water-nsoluble silicone conditioning agent. The silicone conditioning agent may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 5,000 to about 1,500,000 csk, more preferably from about 10,000 to about 1,000,000 csk.

In an opaque composition embodiment of the present invention, the personal care composition comprises a non-volatile silicone oil having a particle size as measured in the personal care composition from about 1 μm to about 50 μm. In an embodiment of the present invention for small particle application to the hair, the personal care composition comprises a non-volatile silicone oil having a particle size as measured in the personal care composition from about 100 nm to about 1 μm. A substantially clear composition embodiment of the present invention comprises a non-volatile silicone oil having a particle size as measured in the personal care composition of less than about 100 nm.

Non-volatile silicone oils suitable for use in compositions of the present invention may be selected from organo-modified silicones and fluoro-modified silicones. In one embodiment of the present invention, the non-volatile silicone oil is an organo-modified silicone which comprises an organo group selected from the group consisting of alkyl groups, alkenyl groups, hydroxyl groups, amine groups, quaternary groups, carboxyl groups, fatty acid groups, ether groups, ester groups, mercapto groups, sulfate groups, sulfonate groups, phosphate groups, propylene oxide groups, and ethylene oxide groups.

In a preferred embodiment of the present invention, the non-volatile silicone oil is dimethicone.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984).

2. Organic Conditioning Oils

The oily conditioning agent of the compositions of the present invention may also comprise at least one organic conditioning oil, either alone or in combination with other conditioning agents, such as the silicones described above.

a. Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include 2,2,4,4,6,6,8,8-dimethyl-10-methylundecane and 2,2,4,4,6,6-dimethyl-8-methylnonane, available from Permethyl Corporation. A preferred hydrocarbon polymer is polybutene, such as the copolymer of isobutylene and butene, which is commercially available as L-14 polybutene from Amoco Chemical Corporation.

b. Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents.

c. Fatty Esters

Other suitable organic conditioning oils for use as the conditioning agent in the compositions of the present invention include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are those known as polyhydric alcohol esters. Such polyhydric alcohol esters include alkylene glycol esters.

Still other fatty esters suitable for use in the compositions of the present invention are glycerides, including, but not limited to, mono-, di-, and tri-glycerides, preferably di- and tri-glycerides, more preferably triglycerides. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

d. Fluorinated Conditioning Compounds

Fluorinated compounds suitable for delivering conditioning to hair or skin as organic conditioning oils include perfluoropolyethers, perfluorinated olefins, fluorine based specialty polymers that may be in a fluid or elastomer form similar to the silicone fluids previously described, and perfluorinated dimethicones. Specific non-limiting examples of suitable fluorinated compounds include the Fomblin product line from Ausimont which includes HC/04, HC/25, HC01, HC/02, HC/03; Dioctyldodecyl Fluoroeptyl Citrate, commonly called Biosil Basics Fluoro Gerbet 3.5 supplied by Biosil Technologies; and Biosil Basics Fluorosil LF also supplied by Biosil Technologies.

e. Fatty Alcohols

Other suitable organic conditioning oils for use in the personal care compositions of the present invention include, but are not limited to, fatty alcohols having at least about 10 carbon atoms, more preferably about 10 to about 22 carbon atoms, most preferably about 12 to about 16 carbon atoms. Also suitable for use in the personal care compositions of the present inventions are alkoxylated fatty alcohols which conform to the general formula:

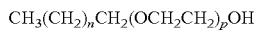

$$CH_3(CH_2)_nCH_2(OCH_2CH_2)_pOH$$

wherein n is a positive integer having a value from about 8 to about 20, preferably about 10 to about 14, and p is a positive integer having a value from about 1 to about 30, preferably from about 2 to about 23.

f. Alkyl Glucosides and Alkyl Glucoside Derivatives

Suitable organic conditioning oils for use in the personal care compositions of the present invention include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

3. Other Conditioning Agents a. Quaternary Ammonium Compounds

Suitable quaternary ammonium compounds for use as conditioning agents in the personal care compositions of the present invention include, but are not limited to, hydrophilic quaternary ammonium compounds with a long chain substituent having a carbonyl moiety, like an amide moiety, or a phosphate ester moiety or a similar hydrophilic moiety.

Examples of useful hydrophilic quaternary ammonium compounds include, but are not limited to, compounds designated in the CTFA Cosmetic Dictionary as ricinoleamidopropyl trimonium chloride, ricinoleamido trimonium ethylsulfate, hydroxy stearamidopropyl trimoniummethylsulfate and hydroxy stearamidopropyl trimonium chloride, or combinations thereof.

Examples of other useful quaternary ammonium surfactants include, but are not limited to, Quaternium-33, Quaternium-43, isostearamidopropyl ethyldimonium ethosulfate, Quaternium-22 and Quaternium-26, or combinations thereof, as designated in the CTFA Dictionary.

Other hydrophilic quaternary ammonium compounds useful in a composition of the present invention include, but are not limited to, Quaternium-16, Quaternium-27, Quaternium-30, Quaternium-52, Quaternium-53, Quaternium-56, Quaternium-60, Quaternium-61, Quaternium-62, Quaternium-63, Quaternium-71, and combinations thereof.

b. Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

E. Additional Components

The personal care compositions of the present invention may further comprise one or more additional components known for use in hair care or personal care products, provided that the additional components are physically and chemically compatible with the essential components described herein, or do not otherwise unduly impair product stability, aesthetics or performance. Individual concentrations of such additional components may range from about 0.001% to about 10% by weight of the personal care compositions.

Non-limiting examples of additional components for use in the composition include natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

1. Cellulose or Guar Cationic Deposition Polymers

The personal care compositions of the present invention may also include cellulose or guar cationic deposition polymers. Generally, such cellulose or guar cationic deposition polymers may be present at a concentration from about 0.05% to about 5%, by weight of the composition. Suitable cellulose or guar cationic deposition polymers have a molecular weight of greater than about 5,000. Additionally, such cellulose or guar deposition polymers have a charge density from about 0.5 meq/g to about 4.0 meq/g at the pH of intended use of the personal care composition, which pH will generally range from about pH 3 to about pH 9, preferably between about pH 4 and about pH 8. The pH of the compositions of the present invention are measured neat.

Suitable cellulose or guar cationic polymers include those which conform to the following formula:

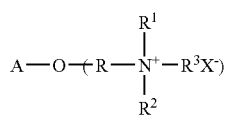

wherein A is an anhydroglucose residual group, such as a cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less; and X is an anionic counterion. Non-limiting examples of such counterions include halides (e.g., chlorine, fluorine, bromine, iodine), sulfate and methylsulfate. The degree of cationic substitution in these polysaccharide polymers is typically from about 0.01 to about 1 cationic groups per anhydroglucose unit.

In one embodiment of the invention, the cellulose or guar cationic polymers are salts of hydroxyethyl cellulose reacted with trimethyl ammonium substituted epoxide, referred to in the industry (CTFA) as Polyquaternium 10 and available from Amerchol Corp. (Edison, N.J., USA).

2. Synthetic Cationic Deposition Polymers

The personal care compositions of the present invention may also include synthetic cationic deposition polymers. Generally, such synthetic cationic deposition polymers may be present at a concentration from about 0.025% to about 5%, by weight of the composition. Such synthetic cationic deposition polymers have a molecular weight from about 1,000 to about 5,000,000. Additionally, such synthetic cationic deposition polymers have a charge density from about 0.5 meq/g to about 10 meq/g.

Suitable synthetic cationic deposition polymers include those which are water-soluble or dispersible, cationic, non-crosslinked, conditioning copolymers comprising: (i) one or more cationic monomer units; and (ii) one or more nonionic monomer units or monomer units bearing a terminal negative charge; wherein said copolymer has a net positive charge, a cationic charge density of from about 0.5 meq/g to about 10 meg/g, and an average molecular weight from about 1,000 to about 5,000,000.

Non-limiting examples of suitable synthetic cationic deposition polymers are described in U.S. Patent Application Publication U.S. 2003/0223951 A1 to Geary et al.

3. Anti-Dandruff Actives

The compositions of the present invention may also contain an anti-dandruff active. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the essential components of the composition, and should not otherwise unduly impair product stability, aesthetics or performance.

Pyridinethione anti-microbial and anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

Azole anti-microbials include imidazoles such as climbazole and ketoconazole.

Selenium sulfide compounds are described, for example, in U.S. Pat. No. 2,694,668; U.S. Pat. No. 3,152,046; U.S. Pat. No. 4,089,945; and U.S. Pat. No. 4,885,107.

Sulfur may also be used as a particulate anti-microbial/anti-dandruff agent in the anti-microbial compositions of the present invention.

The present invention may further comprise one or more keratolytic agents such as Salicylic Acid.

Additional anti-microbial actives of the present invention may include extracts of melaleuca (tea tree) and charcoal.

When present in the composition, the anti-dandruff active is included in an amount from about 0.01% to about 5%, preferably from about 0.1% to about 3%, and more preferably from about 0.3% to about 2%, by weight of the composition.

4. Particles

The compositions of the present invention optionally may comprise particles. Particles useful in the present invention can be inorganic, synthetic, or semi-synthetic. In the compositions of the present invention, it is preferable to incorporate no more than about 20%, more preferably no more than about 10% and even more preferably no more than 2%, by weight of the composition, of particles. In an embodiment of the present invention, the particles have an average mean particle size of less than about 300 □m.

Non-limiting examples of inorganic particles include colloidal silicas, fumed silicas, precipitated silicas, silica gels, magnesium silicate, glass particles, talcs, micas, sericites, and various natural and synthetic clays including bentonites, hectorites, and montmorillonites.

Examples of synthetic particles include silicone resins, poly(meth)acrylates, polyethylene, polyester, polypropylene, polystyrene, polyurethane, polyamide (e.g., Nylon®), epoxy resins, urea resins, acrylic powders, and the like.

Non-limiting examples of hybrid particles include sericite & crosslinked polystyrene hybrid powder, and mica and silica hybrid powder.

5. Opacifying Agents

The compositions of the present invention may also contain one or more opacifying agents. Opacifying agents are typically used in cleansing compositions to impart desired aesthetic benefits to the composition, such as color or pearlescence. In the compositions of the present invention, it is preferable to incorporate no more than about 20%, more preferably no more than about 10% and even more preferably no more than 2%, by weight of the composition, of opacifying agents.

Suitable opacifying agents include, for example, fumed silica, polymethylmethacrylate, micronized TEFLON®, boron nitride, barium sulfate, acrylate polymers, aluminum silicate, aluminum starch octenylsuccinate, calcium silicate, cellulose, chalk, corn starch, diatomaceous earth, Fuller's earth, glyceryl starch, hydrated silica, magnesium carbonate, magnesium hydroxide, magnesium oxide, magnesium trisilicate, maltodextrin, microcrystalline cellulose, rice starch, silica, titanium dioxide, zinc laurate, zinc myristate, zinc neodecanoate, zinc rosinate, zinc stearate, polyethylene, alumina, attapulgite, calcium carbonate, calcium silicate, dextran, nylon, silica silylate, silk powder, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature.

The opacifying agents may also comprise various organic and inorganic pigments. The organic pigments are generally various aromatic types including azo, indigoid, triphenylmethane, anthraquinone, and xanthine dyes. Inorganic pigments include iron oxides, ultramarine and chromium or chromium hydroxide colors, and mixtures thereof.

6. Suspending Agents

The compositions of the present invention may further comprise a suspending agent at concentrations effective for suspending water-insoluble material in dispersed form in the compositions or for modifying the viscosity of the composition. Such concentrations generally range from about 0.1% to about 10%, preferably from about 0.3% to about 5.0%, by weight of the composition, of suspending agent.

Suspending agents useful herein include anionic polymers and nonionic polymers. Useful herein are vinyl polymers such as cross linked acrylic acid polymers with the CTFA name Carbomer.

7. Paraffinic Hydrocarbons

The compositions of the present invention may contain one or more paraffinic hydrocarbons. Paraffinic hydrocarbons suitable for use in compositions of the present invention include those materials which are known for use in hair care or other personal care compositions, such as those having a vapor pressure at 1 atm of equal to or greater than about 21° C. (about 70° F.). Non-limiting examples include pentane and isopentane.

8. Propellants

The composition of the present invention also may contain one or more propellants. Propellants suitable for use in compositions of the present invention include those materials which are known for use in hair care or other personal care compositions, such as liquefied gas propellants and compressed gas propellants. Suitable propellants have a vapor pressure at 1 atm of less than about 21° C. (about 70° F.). Non-limiting examples of suitable propellants are alkanes, isoalkanes, haloalkanes, dimethyl ether, nitrogen, nitrous oxide, carbon dioxide, and mixtures thereof.

9. Other Optional Components

The compositions of the present invention may contain fragrance.

The compositions of the present invention may also contain water-soluble and water-insoluble vitamins such as vitamins B1, B2, B6, B12, C, pantothenic acid, pantothenyl ethyl ether, panthenol, biotin and their derivatives, and vitamins A, D, E, and their derivatives. The compositions of the present invention may also contain water-soluble and water-insoluble amino acids such as asparagine, alanine, indole, glutamic acid and their salts, and tyrosine, tryptamine, lysine, histadine and their salts.

The compositions of the present invention may contain a mono- or divalent salt such as sodium chloride.

The compositions of the present invention may also contain chelating agents.

The compositions of present invention may further comprise materials useful for hair loss prevention and hair growth stimulants or agents.

F. Method of Making

The compositions of the present invention, in general, may be made by mixing the ingredients together at either room temperature or at elevated temperature, e.g., about 72° C. Heat only needs to be used if solid ingredients are in the composition. The ingredients are mixed at the batch processing temperature. Additional ingredients, including electrolytes, polymers, fragrance, and particles, may be added to the product at room temperature.

G. Method of Treating Hair or Skin

The personal care compositions of the present invention are used in a conventional manner for cleansing and conditioning hair or skin. Generally, a method of treating hair or skin of the present invention comprises applying the personal care composition of the present invention to the hair or skin. More specifically, an effective amount of the personal care composition is applied to the hair or skin, which has preferably been wetted with water, and then the personal care composition is rinsed off. Such effective amounts generally range from about 1 g to about 50 g, preferably from about 1 g to about 20 g. Application to the hair typically includes working the composition through the hair such that most or all of the hair is contacted with the composition.

This method for treating the hair or skin comprises the steps of: (a) applying an effective amount of the personal care composition to the hair or skin, and (b) rinsing the applied areas of hair or skin with water. These steps can be repeated as many times as desired to achieve the desired cleansing and conditioning benefit.

For use in methods of the present invention, the personal care composition may be in various forms, for example, shampoos, body washes, gels, lotions, creams, mousses, and sprays. For some of these forms, the personal care composition may be packaged in a pump-dispenser bottle or in an aerosol container. In other useful forms, the personal care composition may be dried to a film or a powder, or it may be applied to a substrate which is then used for application to the hair or skin.

Non-Limiting Examples

The compositions illustrated in the following Examples illustrate specific embodiments of the compositions of the present invention, but are not intended to be limiting thereof. Other modifications can be undertaken by the skilled artisan without departing from the spirit and scope of this invention. These exemplified embodiments of the composition of the present invention provide enhanced deposition of conditioning agents to the hair and/or skin.

The compositions illustrated in the following Examples are prepared by conventional formulation and mixing methods, an example of which is described above. All exemplified amounts are listed as weight percents and exclude minor materials such as diluents, preservatives, color solutions, imagery ingredients, botanicals, and so forth, unless otherwise specified.

The following are representative of shampoo compositions of the present invention:

| | The following are representative of shampoo compositions of the present invention: | | | | |
|---|---|---|---|---|---|
| | Examples Without Oily Conditioning Agent | | | | |
| Ingredient | 1 | 2 | 3 | 4 | 5 |
| Water | q.s. | q.s. | q.s. | q.s. | q.s. |
| Catonic Starch[1] | 0.25 | — | 0.25 | — | — |
| Cationic Starch[2] | — | 0.25 | — | 0.50 | — |
| Amphoteric Starch[3] | — | — | — | — | 0.50 |
| Sodium Laureth Sulfate (SLE3S - 29% active)[4] | 48.27 (14.0) | 41.38 (12.0) | 41.38 (12.0) | 51.72 (15.0) | 41.38 (12.0) |
| Sodium Lauryl Sulfate (SLS - 29% active)[5] | 6.90 (2.0) | 6.90 (2.0) | — | 17.24 (5.0) | 6.90 (2.0) |
| Sodium Alkyl Glyceryl Sulfonate (AGS - 47.3% active)[6] | — | — | 6.38 (3.0) | — | — |
| Disodium Coco Amphodiacetate[7] | 5.0 | 5.0 | — | — | 5.0 |
| Cocoamidopropyl Betaine[8] | — | — | 13.3 | — | — |
| PPG-2 Hydroxyethyl Coco/Isostearamide[9] | 2.0 | 2.0 | 2.0 | 2.0 | 2.0 |
| Sodium Chloride[10] | 2.0 | 1.5 | 2.0 | 1.8 | 1.5 |
| Fragrance | 0.70 | 0.70 | 0.70 | 0.70 | 0.70 |
| Preservatives, pH adjusters | <1% | <1% | <1% | <1% | <1% |
| Calculated: | | | | | |
| Ethoxylate level | 4.12 | 3.53 | 4.12 | 4.41 | 3.53 |
| Sulfate level | 3.17 | 2.79 | 2.26 | 4.16 | 2.79 |
| Sulfonate level | — | — | 1.47 | — | — |
| Anion level | 3.17 | 2.79 | 3.73 | 4.16 | 2.79 |

[1]Cationic Starch, MW = 25,200; DS = 0.50; CD = 2.1 meq/g
[2]Cationic Starch, MW = 79,600; DS = 0.65; CD = 2.5 meq/g
[3]Amphoteric Starch, MW = 85,000; Quat DS = 0.5 meq/g; Anionic DS = 0.5 meq/g
[4]Sodium Laureth Sulfate at 29% active, supplier: P&G
[5]Sodium Lauryl Sulfate at 29% active, supplier: P&G
[6]Sodium Alkyl Glyceryl Sulfonate at 47.3% active (AGS-1214), supplier: P&G
[7]Miranol C2M Conc NP, 40% active, supplier: Rhodia.
[8]Tegobetaine F-B, 30% active, supplier: Goldschmidt Chemicals
[9]Promidium 2, supplier Unichema
[10]Sodium Chloride USP (food grade), supplier Morton.

| | Examples with 30 nm Silicone Particles | | | | | | | |
|---|---|---|---|---|---|---|---|---|
| Ingredient | 6 | 7 | 8 | 9 | 10 | 11 | 12 | 13 |
| Water | q.s. | q.s. | q.s. | q.s. | q.s. | q.s. | q.s. | q.s. |
| Cationic Starch[1] | 0.25 | 0.25 | 0.25 | 0.25 | 0.25 | 0.25 | — | — |
| Cationic Starch[2] | — | — | — | — | — | — | 0.25 | — |
| Amphoteric Starch[3] | — | — | — | — | — | — | — | 0.25 |
| Sodium Laureth Sulfate (SLE3S - 29% active)[4] | 48.27 (14.0) | 48.27 (14.0) | 48.27 (14.0) | 48.27 (14.0) | 41.38 (12.0) | 48.27 (14.0) | 34.48 (10.0) | 41.38 (12.0) |
| Sodium Lauryl Sulfate (SLS - 29% active)[5] | 6.90 (2.0) | 6.90 (2.0) | 6.90 (2.0) | 6.90 (2.0) | 6.90 (2.0) | 6.90 (2.0) | 6.90 (2.0) | 6.90 (2.0) |
| Dimethiconol Microemulsion A[6] | 4.0 | — | — | — | 2.0 | — | 4.0 | 2.0 |
| Dimethiconol Microemulsion B[7] | — | 4.0 | — | — | — | — | — | — |
| Dimethiconol Microemulsion C[8] | — | — | 4.0 | — | — | — | — | — |
| Dimethiconol Microemulsion D[9] | — | — | — | 4.0 | — | — | — | — |
| Disodium Coco Amphodiacetate[10] | 5.0 | 5.0 | 5.0 | 5.0 | — | — | 5.0 | 5.0 |
| Cocoamdopropyl Betaine[11] | — | — | — | — | 6.7 | — | — | — |
| PPG-2 Hydroxyethyl Coco/Isostearamide[12] | 2.0 | 2.0 | 2.0 | 2.0 | — | 2.0 | — | 2.0 |
| Cocamide MEA[13] | — | — | — | — | — | — | 0.8 | — |
| Sodium Chloride[14] | 2.0 | 2.0 | 2.0 | 2.0 | 1.8 | 2.4 | 1.8 | 2.0 |

-continued

| | | | | | | | | |
|---|---|---|---|---|---|---|---|---|
| Fragrance | 0.70 | 0.70 | 0.70 | 0.70 | 0.70 | 0.70 | 0.70 | 0.70 |
| Preservatives, pH adjusters | <1% | <1% | <1% | <1% | <1% | <1% | <1% | <1% |
| Calculated: | | | | | | | | |
| Ethoxylate level | 4.12 | 4.12 | 4.12 | 4.12 | 3.53 | 4.12 | 2.94 | 3.53 |
| Anion level | 3.17 | 3.17 | 3.17 | 3.17 | 2.79 | 3.17 | 2.42 | 2.79 |

[1]Cationic Starch, MW = 25,200; DS = 0.50; CD = 2.1 meq/g
[2]Cationic Starch, MW = 79,600; DS = 0.65; CD = 2.5 meq/g
[3]Amphoteric Starch, MW = 85,000; Quat DS = 0.5 meg/g; Anionic DS = 0.5 meq/g
[4]Sodium Laureth Sulfate at 29% active, supplier: P&G
[5]Sodium Lauryl Sulfate at 29% active, supplier: P&G
[6]Dow Corning Silicone Micro-emulsion DC-1870; Internal Phase Viscosity = 72,000; 30 nm particle size dimethiconol using TEA dodecyl benzene sulfonate and laureth 23 as primary surfactants, 25% active silicone
[7]Dow Corning Sample 2-1865; Internal Phase Viscosity = 44,000 cps; 30 nm particle size dimethiconol using TEA dodecyl benzene sulfonate and laureth 23 as primary surfactants, 25% active silicone
[8]Dow Corning Sample 2-1865; Internal Phase Viscosity = 34,000 cps; 30 nm particle size dimethiconol using TEA dodecyl benzene sulfonate and laureth 23 as primary surfactants, 25% active.
[9]Microemulsion, Internal Phase Viscosity = 25,400 cps; 30 nm particle size dimethiconol, <1% D4 achieved through a Dow Corning Steam Stripping process, 25% active silicone, supplier: Dow Corning
[10]Miranol C2M Conc NP, 40% active, supplier: Rhodia.
[11]Tegobetaine F-B, 30% active, supplier: Goldschmidt Chemicals
[12]Promidium 2, supplier Unichema
[13]Monamid CMA, supplier Goldschmidt Chemical
[14]Sodium Chloride USP (food grade), supplier Morton.

| | Examples with 300 nm Silicone Particles | | | | | |
|---|---|---|---|---|---|---|
| Ingredient | 14 | 15 | 16 | 17 | 18 | 19 |
| Water | q.s. | q.s. | q.s. | q.s. | q.s. | q.s. |
| Catonic Starch[1] | 0.25 | | 0.25 | | 0.25 | |
| Cationic Starch[2] | | 0.25 | | 0.25 | | 0.25 |
| Sodium Laureth Sulfate (SLE3S - 29% active)[3] | 48.27 (14.0) | 48.27 (14.0) | 48.27 (14.0) | 41.38 (12.0) | 41.38 (12.0) | 34.48 (10.0) |
| Sodium Lauryl Sulfate (SLS - 29% active)[4] | 6.90 (2.0) | 6.90 (2.0) | 6.90 (2.0) | 6.90 (2.0) | 6.90 (2.0) | 6.90 (2.0) |
| Dimethicone Emulsion[5] | 2.0 | 2.0 | 2.0 | 2.0 | 1.0 | 4.0 |
| Disodium Coco Amphodiacetate[6] | 5.0 | 5.0 | 5.0 | — | — | 5.0 |
| Cocoamdopropyl Betaine[7] | — | — | — | 6.7 | — | — |
| PPG-2 Hydroxyethyl Coco/Isostearamide[8] | 2.0 | 2.0 | 2.0 | 2.0 | 2.0 | 2.0 |
| Ethylene Glycol Distearate[9] | — | — | 1.50 | — | — | — |
| Sodium Chloride[10] | 2.0 | 1.5 | 1.5 | 1.8 | 2.4 | 1.8 |
| Fragrance | 0.70 | 0.70 | 0.70 | 0.70 | 0.70 | 0.70 |
| Preservatives, pH adjusters | <1% | <1% | <1% | <1% | <1% | <1% |
| Calculated: | | | | | | |
| Ethoxylate level | 4.12 | 4.12 | 4.12 | 3.53 | 3.53 | 2.94 |
| Anion level | 3.17 | 3.17 | 3.17 | 2.79 | 2.79 | 2.42 |

[1]Cationic Starch, MW = 25,200; DS = 0.50; CD = 2.1 meq/g
[2]Cationic Starch, MW = 79,600; DS = 0.65; CD = 2.5 meq/g
[3]Sodium Laureth Sulfate at 29% active, supplier: P&G
[4]Sodium Lauryl Sulfate at 29% active, supplier: P&G
[5]Dow Corning Dimethicone emulsion DC-1664; 3 micron particle size; 50% active
[6]Miranol C2M Conc NP, 40% active, supplier: Rhodia.
[7]Tegobetaine F-B, 30% active, supplier: Goldschmidt Chemicals
[8]Promidium 2, supplier Unichema
[9]Ethylene Glycol Distearate, EGDS Pure, supplier Goldschmidt Chemical
[10]Sodium Chloride USP (food grade), supplier Morton

| | Examples with 30 micron avg. Silicone Particles | | | | | | |
|---|---|---|---|---|---|---|---|
| Ingredient | 20 | 21 | 22 | 23 | 24 | 25 | 26 |
| Water | q.s. | q.s. | q.s. | q.s. | q.s. | q.s. | q.s. |
| Catonic Starch[1] | 0.25 | — | 0.25 | — | 0.25 | 0.25 | — |
| Cationic Starch[2] | — | 0.25 | — | 0.25 | — | — | 0.25 |
| Sodium Laureth Sulfate (SLE3S - 29% active)[3] | 48.27 (14.0) | 48.27 (14.0) | 48.27 (14.0) | 41.38 (12.0) | 41.38 (12.0) | 34.48 (10.0) | 34.48 (10.0) |

-continued

| Ingredient | | | | | | | |
|---|---|---|---|---|---|---|---|
| Sodium Lauryl Sulfate (SLS - 29% active)[4] | 6.90 (2.0) | 6.90 (2.0) | 6.90 (2.0) | 6.90 (2.0) | 6.90 (2.0) | 6.90 (2.0) | 20.69 (6.0) |
| Dimethicone Gum[5] | 1.0 | 1.0 | 0.5 | 1.0 | 1.0 | 1.0 | 1.0 |
| Disodium Coco Amphodiacetate[6] | 5.0 | 5.0 | 5.0 | — | — | 5.0 | — |
| Cocoamdopropyl Betaine[7] | — | — | — | 6.7 | — | — | 6.7 |
| PPG-2 Hydroxyethyl Coco/Isostearamide[8] | 2.0 | 2.0 | 2.0 | 2.0 | 2.0 | 2.0 | 2.0 |
| Ethylene Glycol Distearate[9] | 1.5 | 1.5 | 1.50 | 1.5 | 1.5 | 1.5 | 1.5 |
| Sodium Chloride[10] | 1.5 | 1.2 | 1.5 | 1.7 | 2.0 | 1.8 | 1.0 |
| Fragrance | 0.70 | 0.70 | 0.70 | 0.70 | 0.70 | 0.70 | 0.70 |
| Preservatives, pH adjusters | <1% | <1% | <1% | <1% | <1% | <1% | <1% |
| Calculated: | | | | | | | |
| Ethoxylate level | 4.12 | 4.12 | 4.12 | 3.53 | 3.53 | 2.94 | 2.94 |
| Anion level | 3.17 | 3.17 | 2.64 | 2.79 | 2.79 | 2.42 | 3.48 |

[1] Cationic Starch, MW = 25,200; DS = 0.50; CD = 2.1 meq/g
[2] Cationic Starch, MW = 79,600; DS = 0.65; CD = 2.5 meq/g
[3] Sodium Laureth Sulfate at 29% active, supplier: P&G
[4] Sodium Lauryl Sulfate at 29% active, supplier: P&G
[5] Dimethicone Gum Viscasil 330 M; 3 micron particle size; 50% active, supplier General Electric
[6] Miranol C2M Conc NP, 40% active, supplier: Rhodia.
[7] Tegobetaine F-B, 30% active, supplier: Goldschmidt Chemicals
[8] Promidium 2, supplier Unichema
[9] Ethylene Glycol Distearate, EGDS Pure, supplier Goldschmidt Chemical
[10] Sodium Chloride USP (food grade), supplier Morton.

| | Examples with Cationic Starch and Guar or Cellulose | | | | | | |
|---|---|---|---|---|---|---|---|
| Ingredient | 27 | 28 | 29 | 30 | 31 | 32 | 33 |
| Water | q.s. | q.s. | q.s. | q.s. | q.s. | q.s. | q.s. |
| Catonic Starch[1] | 0.25 | 0.25 | 0.25 | 0.25 | 0.25 | 0.25 | — |
| Cationic Starch[2] | — | — | — | — | — | — | 0.25 |
| Cationic Cellulose Polymer[3] | 0.10 | — | — | — | 0.10 | — | 0.10 |
| Polyquaterium 10[4] | — | 0.10 | — | — | — | — | — |
| Polyquaterium 10[5] | — | — | 0.10 | — | — | — | — |
| Guar Hydroxypropyl Trimonium Chloride[6] | — | — | — | 0.10 | — | — | — |
| Sodium Laureth Sulfate (SLE3S - 29% active)[7] | 41.38 (12.0) | 41.38 (12.0) | 41.38 (12.0) | 41.38 (12.0) | 48.27 (14.0) | 48.27 (14.0) | 41.38 (12.0) |
| Sodium Lauryl Sulfate (SLS - 29% active)[8] | 6.90 (2.0) | 6.90 (2.0) | 6.90 (2.0) | 6.90 (2.0) | 6.90 (2.0) | 6.90 (2.0) | 6.90 (2.0) |
| Dimethiconol Microemulsion A[9] | 4.0 | — | — | — | 2.0 | 4.0 | 4.0 |
| Dimethiconol Microemulsion B[10] | — | 4.0 | — | — | — | — | — |
| Dimethiconol Microemulsion C[11] | — | — | 4.0 | — | — | — | — |
| Dimethiconol Microemulsion C[12] | — | — | — | 4.0 | — | — | — |
| Disodium Coco Amphodiacetate[13] | 5.0 | 5.0 | 5.0 | 5.0 | 5.0 | — | 5.0 |
| Cocoamdopropyl Betaine[14] | — | — | — | — | — | 6.7 | — |
| PPG-2 Hydroxyethyl Coco/Isostearamide[15] | 2.0 | 2.0 | 2.0 | 2.0 | 2.0 | 2.0 | 2.0 |
| Sodium Chloride[16] | 2.0 | 2.0 | 2.0 | 2.0 | 1.8 | 2.4 | 1.8 |
| Fragrance | 0.70 | 0.70 | 0.70 | 0.70 | 0.70 | 0.70 | 0.70 |
| Preservatives, pH adjusters | <1% | <1% | <1% | <1% | <1% | <1% | <1% |

-continued

| Calculated: | | | | | | | |
|---|---|---|---|---|---|---|---|
| Ethoxylate level | 3.53 | 3.53 | 3.53 | 3.53 | 4.12 | 4.12 | 3.53 |
| Anion level | 2.79 | 2.79 | 2.79 | 2.79 | 3.17 | 3.17 | 2.79 |

[1] Cationic Starch, MW = 25,200; DS = 0.50; CD = 2.1 meq/g
[2] Cationic Starch, MW = 79,600; DS = 0.65; CD = 2.5 meq/g
[3] Polyquaterium 10 polymer with MW = 2.0 MM and charge density = 0.7
[4] UCare Polymer JR30M, MW = 2.0 MM, charge density = 1.32 meq/g, supplier Dow Chemicals
[5] UCare Polymer KG30M, MW = 2.0 MM, charge density = 1.96 meq/g, supplier Dow Chemicals
[6] Jaguar Excel, supplier: Rhodia.
[7] Sodium Laureth Sulfate at 29% active, supplier: P&G
[8] Sodium Lauryl Sulfate at 29% active, supplier: P&G
[9] Dow Corning Silicone Micro-emulsion DC-1870; Internal Phase Viscosity = 72,000; 30 nm particle size dimethiconol using TEA dodecyl benzene sulfonate and laureth 23 as primary surfactants, 25% active silicone
[10] Dow Corning Sample 2-1865; Internal Phase Viscosity = 44,000 cps; 30 nm particle size dimethiconol using TEA dodecyl benzene sulfonate and laureth 23 as primary surfactants, 25% active silicone
[11] Dow Corning Sample 2-1865; Internal Phase Viscosity = 34,000 cps; 30 nm particle size dimethiconol using TEA dodecyl benzene sulfonate and laureth 23 as primary surfactants, 25% active.
[12] Microemulsion, Internal Phase Viscosity = 25,400 cps; 30 nm particle size dimethiconol, <1% D4 achieved through a Dow Corning Steam Stripping process, 25% active silicone, supplier: Dow Corning
[13] Miranol C2M Conc NP, 40% active, supplier: Rhodia.
[14] Tegobetaine F-B, 30% active, supplier: Goldschmidt Chemicals
[15] Promidium 2, supplier Unichema
[16] Sodium Chloride USP (food grade), supplier Morton.

| | Examples with Optional Components | | | | |
|---|---|---|---|---|---|
| Ingredient | 34 | 35 | 36 | 37 | 38 |
| Water | q.s. | q.s. | q.s. | q.s. | q.s. |
| Catonic Starch[1] | 0.25 | 0.50 | — | 0.50 | 0.25 |
| Cationic Starch[2] | — | — | 0.50 | — | — |
| Sodium Laureth Sulfate (SLE3S - 29% active)[3] | 48.27 (14.0) | 48.27 (14.0) | 41.38 (12.0) | 48.27 (14.0) | 48.27 (14.0) |
| Sodium Lauryl Sulfate (SLS - 29% active)[4] | 6.90 (2.0) | 6.90 (2.0) | 6.90 (2.0) | 6.90 (2.0) | 6.90 (2.0) |
| Aminosilicone[5] | — | — | — | 2.0 | — |
| Aminosilicone[6] | — | — | — | — | 2.0 |
| Di-PPG-2 Myreth-10 Adipate[7] | 1.0 | — | — | — | — |
| Cocamide MEA[8] | — | — | 0.80 | — | — |
| Disodium Coco Amphodiacetate[9] | 5.0 | 5.0 | 5.0 | 5.0 | 5.0 |
| Precipitated Silica[10] | — | 1.0 | 1.0 | 1.0 | 1.0 |
| PPG-2 Hydroxyethyl Coco/Isostearamide[11] | 2.0 | 2.0 | — | 2.0 | 2.0 |
| Ethylene Glycol Distearate[12] | 1.5 | 1.5 | 1.5 | 1.5 | 1.5 |
| Sodium Chloride[13] | 1.5 | 1.5 | 1.5 | 1.5 | 1.5 |
| Fragrance | 0.70 | 0.70 | 0.70 | 0.70 | 0.70 |
| Preservatives, pH adjusters | <1% | <1% | <1% | <1% | <1% |
| Calculated: | | | | | |
| Ethoxylate level | 4.12 | 4.12 | 3.53 | 4.12 | 4.12 |
| Anion level | 3.17 | 3.17 | 2.79 | 3.17 | 3.17 |

[1] Cationic Starch, MW = 25,200; DS = 0.50; CD = 2.1 meq/g
[2] Cationic Starch, MW = 79,600; DS = 0.65; CD = 2.5 meq/g
[3] Sodium Laureth Sulfate at 29% active, supplier: P&G
[4] Sodium Lauryl Sulfate at 29% active, supplier: P&G
[5] Aminosilicone; supplier General Electric; terminal aminopropyl substitution, viscosity 350,000, D~1600, M' = 2, particle size 3 μm
[6] DC 2-8194 Aminosilicone; supplier Dow Corning, particle size ~30 nm
[7] Cromollient SCE, supplier Croda
[8] Monamid CMA, supplier Goldschmidt Chemical
[9] Miranol C2M Conc NP, 40% active, supplier: Rhodia.
[10] Tegobetaine F-B, 30% active, supplier: Goldschmidt Chemical
[11] Promidium 2, supplier Unichema
[12] Ethylene Glycol Distearate, EGDS Pure, supplier Goldschmidt Chemical
[13] Sodium Chloride USP (food grade), supplier Morton The following are representative of body wash
compositions of the present invention:

| Ingredient | Examples with Oily Conditioning Agents | | | |
|---|---|---|---|---|
| | 39 | 40 | 41 | 42 |
| Water | q.s. | q.s. | q.s. | q.s. |
| Cationic Starch[1] | 0.25 | 0.25 | 0.25 | 0.5 |
| Polymer JP[2] | 0.25 | | | |
| Polymer KG30M[3] | | 0.5 | | |
| Sodium Laureth Sulfate (SLE3)[4] | 41.38 | 41.38 | 41.38 | 41.38 |
| Sodium Lauryl Sulfate[5] | 6.9 | 13.79 | 6.9 | 6.9 |
| Silicone Microemulsion[6] | 2.0 | | 1.0 | |
| Cetyl Alcohol[7] | | 0.5 | | |
| Disodium Laureth Sulfosuccinate[8] | 1.0 | | | |
| Glycerine[9] | 1.0 | | 2.0 | |
| Cocoamdopropyl Betaine[10] | 3.0 | | | |
| Disodium Coco Amphodiacetate[11] | | 4.44 | 1.0 | 4.44 |
| Decyl Glucoside[12] | | 1.0 | | |
| Glyceryl Stearate, Cetearyl Alcohol, Stearic Acid, 1-Propanamimium-3-Amino-N-(2-hydroxyethyl)N,N-Dimethyl-N-C16-18 Acryl Derivs., Chlorides[13] | | | 0.5 | |
| Perfluoropolymethylisopropyl Ether[14] | | | | 1.0 |
| Magnesium Chloride, hexahydrate[15] | 0.5 | | | |
| Sodium Chloride[16] | 0.55 | 0.6 | 1.0 | 0.6 |
| Fragrance | 0.55 | 0.55 | 0.55 | 0.55 |
| Preservatives, pH adjusters | <1.0 | <1.0 | <1.0 | <1.0 |
| Calculated: | | | | |
| Ethoxylate level | 3.53 | 3.53 | 3.53 | 3.53 |
| Anion level | 2.79 | 3.33 | 2.79 | 2.79 |

[1]Cationic Starch, MW = 79,600; DS = 0.65; CD = 2.5 meq/g
[2]UCare Polymer JP, MW = 2.0 MM, charge density = 0.7 meq./gram, supplier Dow Chemicals
[3]UCare Polymer KG30M, MW = 2.0 MM, charge density = 1.96 meq./gram, supplier Dow Chemicals
[4]Sodium Laureth Sulfate at 29% active with an average of approximately 3 moles of ethoxylation, supplier: P&G
[5]Sodium Lauryl Sulfate at 29% active, supplier: P&G
[6]DC2-1870, 30 nm particle size dimethicone using TEA dodecyl benzene sulfonte and POE lauryl ether as primary surfactants, supplier Dow Corning.
[7]CO-1695, supplier P&G
[8]Stepan-MILD LSB, supplier Steppan
[9]Star, supplier: P&G
[10]Tegobetaine (30% active), supplier Goldschmidt (Degussa)
[11]Schercoteric MS-2 at 45% active, supplier Scher Chemicals, Inc.
[12]Plantaren PS-100, supplier Cognis Care Chemicals
[13]Prolipid 151, supplier ISP
[14]Promidium 2, supplier Unichema
[15]Fomblin HC/04, supplier Ausimont
[16]Magnesium Chloride 6-Hexahydrate, supplier Fisher Chemicals
[17]Sodium Chloride USP (food grade), supplier Morton.

All documents cited herein are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:
1. A shampoo composition comprising:
   a) from about 0.01 wt. % to about 10 wt. % of a water-soluble cationically modified starch polymer, wherein said water-soluble cationically modified starch polymer has a molecular weight from about 1,000 to about 200,000 and a charge density from about 0.7 meq/g to about 2.5 meq/g; wherein said water-soluble cationically modified starch polymer comprises maltodextrin and has a Dextrose Equivalent of less than 35;
   b) from about 5 wt. % to about 50 wt. % of an anionic surfactant system, said anionic surfactant system comprising at least one anionic surfactant and having an ethoxylate level and an anion level,
      i) wherein said anionic surfactant is selected from the group consisting of sodium laureth sulfate, sodium lauryl sulfate, and mixtures thereof,
      ii) wherein said ethoxylate level is from about 2 to about 5, and
      iii) wherein said anion level is from about 2 to about 4;
   c) from about 0.025 wt. % to about 5 wt. % of a second cationic deposition polymer selected from the group consisting of cationic guar, cationic cellulose, synthetic cationic deposition polymers, and mixtures thereof, i) wherein said cationic guar and cationic cellulose have a molecular weight greater than about 200,000 and a charge density from about 0.15 meq/g to about 4.0 meq/g, and ii) wherein said synthetic cationic deposition polymer has a molecular weight from about 1,000 to about 5,000,000 and a charge density from about 2 meq/g to about 10 meq/g; and d) a cosmetically acceptable medium.

2. A shampoo composition according to claim 1, wherein said water-soluble cationically modified starch polymer has a molecular weight from about 5,000 to about 100,000.

3. A shampoo composition according to claim 1, further comprising one or more surfactants selected from the group consisting of amphoteric surfactants, zwitterionic surfactants, cationic surfactants, and nonionic surfactants.

4. A shampoo composition according to claim 1, wherein said cationic cellulose or cationic guar has a charge density from about ¼ to about ½ of the charge density of said water-soluble cationically modified starch polymer.

5. A shampoo composition according to claim 1, further comprising one or more additional components selected from the group consisting of dispersed water-insoluble particles, opacifying agents, suspending agents, anti-dandruff agents, non-volatile paraffinic hydrocarbons, and propellants.

6. A shampoo composition comprising:

a) from about 0.01 wt. % to about 10 wt. % of a water-soluble cationically modified starch polymer, wherein said water-soluble cationically modified starch polymer has a molecular weight from about 1,000 to about 200,000 and a charge density from about 0.7 meq/g to about 2.5 meq/g; wherein said water-soluble cationically modified starch polymer comprises maltodextrin and has a Dextrose Equivalent of less than 35;

b) from about 5 wt. % to about 50 wt. % of an anionic surfactant system, said anionic surfactant system comprising at least one anionic surfactant and having an ethoxylate level and an anion level,
i) wherein said anionic surfactant system is selected from the group consisting of sodium laureth sulfate, sodium lauryl sulfate, and mixtures thereof,
ii) wherein said ethoxylate level is from about 2 to about 5, and
iii) wherein said anion level is from about 2 to about 4; and c) from about 0.01 wt. % to about 10 wt. % of one or more oily conditioning agents;

d) from about 0.025 wt. % to about 5 wt. % of a second cationic deposition polymer selected from the group consisting of cationic guar, cationic cellulose, synthetic cationic deposition polymers, and mixtures thereof,
i) wherein said cationic guar and cationic cellulose have a molecular weight greater than about 200,000 and a charge density from about 0.15 meq/g to about 4.0 meq/g, and
ii) wherein said synthetic cationic deposition polymer has a molecular weight from about 1,000 to about 5,000,000 and a charge density from about 2 meq/g to about 10 meq/g; and e) a cosmetically acceptable medium.

7. A shampoo composition according to claim 6, wherein the ratio of said oily conditioning agent to said water-soluble cationically modified starch polymer is at least 2:1.

8. A shampoo composition according to claim 6, wherein said oily conditioning agent is selected from the group consisting of non-volatile silicone oils, hydrocarbon oils, polyolefins, fatty esters, fluorinated conditioning compounds, and mixtures thereof.

9. A shampoo composition according to claim 8, wherein said non-volatile silicone oil has a particle size as measured in said shampoo composition from about 1 μm to about 50 μm.

10. A shampoo composition according to claim 8, wherein said non-volatile silicone oil has a particle size as measured in said shampoo composition from about 100 nm to about 1 μm.

11. A shampoo composition according to claim 8, wherein said non-volatile silicone oil has a particle size as measured in said shampoo composition of less than 100 nm.

12. A shampoo composition according to claim 8, wherein said non-volatile silicone oil is selected from the group consisting of organo-modified silicones and fluoro-modified silicones.

13. A shampoo composition according to claim 12, wherein said organo-modified silicone comprises an organo group selected from the group consisting of alkyl groups, alkenyl groups, hydroxyl groups, amine groups, quaternary groups, carboxyl groups, fatty acid groups, ether groups, ester groups, mercapto groups, sulfate groups, sulfonate groups, phosphate groups, propylene oxide groups, and ethylene oxide groups.

14. A method of treating hair or skin, said method comprising the steps of:

a) applying a shampoo composition according to claim 1 to said hair or skin; and b) rinsing said hair or skin with water.

* * * * *